US00PP25736P2

(12) United States Plant Patent
Probst

(10) Patent No.: US PP25,736 P2
(45) Date of Patent: Jul. 21, 2015

(54) ***COREOPSIS* PLANT NAMED 'RED SATIN'**

(50) Latin Name: ***Coreopsis* hybrid**
Varietal Denomination: Red Satin

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 100 days.

(21) Appl. No.: 13/998,643

(22) Filed: Nov. 19, 2013

(51) Int. Cl.
*A01H 5/02* (2006.01)

(52) U.S. Cl.
USPC ..... Plt./417

(58) Field of Classification Search
USPC ..... Plt./417
See application file for complete search history.

*Primary Examiner* — Susan McCormick Ewoldt
(74) *Attorney, Agent, or Firm* — Penny J. Aguirre

(57) ABSTRACT

A new cultivar of hybrid *Coreopsis* named 'Red Satin' characterized by its sturdy and upright plant habit, its inflorescences with ray florets that are dark red in color, its thread-like foliage, its production of underground rhizomes that survive conditions of typical U.S.D.A. Zone 5 winters when planted in the landscape, and its sterile inflorescences and due to the lack of seed production; the plants remain relatively resistant to powdery mildew longer into the season than is typical for cultivars of thread-leaf type *Coreopsis*.

2 Drawing Sheets

Botanical classification: *Coreopsis* hybrid.
Variety denomination: 'Red Satin'.

BACKGROUND OF THE INVENTION

The present invention relates to a new and distinct cultivar of *Coreopsis* plant of hybrid origin and botanically known as *Coreopsis* 'Red Satin'. The new cultivar will be referred to hereafter by its cultivar name 'Red Satin'. 'Red Satin' is a herbaceous perennial grown for landscape and container use.

The new invention arose from an ongoing controlled breeding program in Hubbardston, Mass. The objective of the breeding program is to develop hybrid cultivars of *Coreopsis* with unique and superior garden attributes. In particular, to develop cultivars of *Coreopsis* with thread-leaf type foliage that are cold hardy and reliably perennial in U.S.D.A. Zone 5 in a range of flower colors.

The Inventor made a controlled cross in August of 2010 in his test garden in Hubbardston, Mass. between an unnamed proprietary plant from the Inventor's breeding program, reference no. Y2 09-5, as the female parent and pollen that was pooled from unnamed proprietary plants of *Coreopsis* as the male parent. The exact male parent is therefore unknown. 'Red Satin' was selected in July 2011 as a single unique plant amongst the resulting seedlings from the above cross.

Asexual propagation of the new cultivar was first accomplished by stem tip cuttings in Kensington, Conn. in August 2011 under the direction of the Inventor. Asexual propagation by stem tip cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Red Satin' as a unique cultivar of *Coreopsis*.

1. 'Red Satin' exhibits a sturdy, upright plant habit.
2. 'Red Satin' exhibits inflorescences with ray florets that are dark red in color.
3. 'Red Satin' exhibits thread-like foliage (similar to *C. verticillata*).
4. 'Red Satin' exhibits production of underground rhizomes that survive conditions of typical U.S.D.A. Zone 5 winters when planted in the landscape.
5. 'Red Stain' exhibits sterile inflorescences and due to the lack of seed production; the plants remain relatively resistant to powdery mildew longer into the season than is typical for cultivars of thread-leaf type *Coreopsis*.

The female parent of 'Red Satin', Y2 09-5, differs from 'Red Satin' in having flowers that are purple in color, in being taller in height, and in having highly fertile flowers. 'Red Satin' can be most closely compared to the *Coreopsis* cultivars 'Limerock Ruby' (U.S. Plant Pat. No. 15,455) and 'Mercury Rising' (U.S. Plant Pat. No. 24,689). 'Limerock Ruby' is similar to 'Red Satin' in having sterile inflorescences with ray florets that are red in color. 'Limerock Ruby' differs from 'Red Satin' in being taller in height and in being less cold hardy due to a lack of production of underground rhizomes. 'Mercury Rising' is similar to 'Red Satin' in having inflorescences with ray florets that are red in color and in being perennial and cold hardy in U.S.D.A Zone 5. 'Mercury Rising' differs from 'Red Satin' in having leaves that are wider and less dissected (due to some genetic influence of *C. grandiflora*), in having a wider and less upright plant habit, and in having less numerous and larger inflorescences.

BRIEF DESCRIPTION OF THE DRAWINGS

The accompanying colored photographs illustrate the overall appearance and distinct characteristics of the new *Coreopsis*. The photographs in FIG. 1 and FIG. 2 were taken of nine month-old plants of 'Red Satin' as grown outdoors in a one-gallon containter in Hubbardston, Mass.

The photograph in FIG. 1 provides a side view of a plant of 'Red Satin'.

Figure 1:
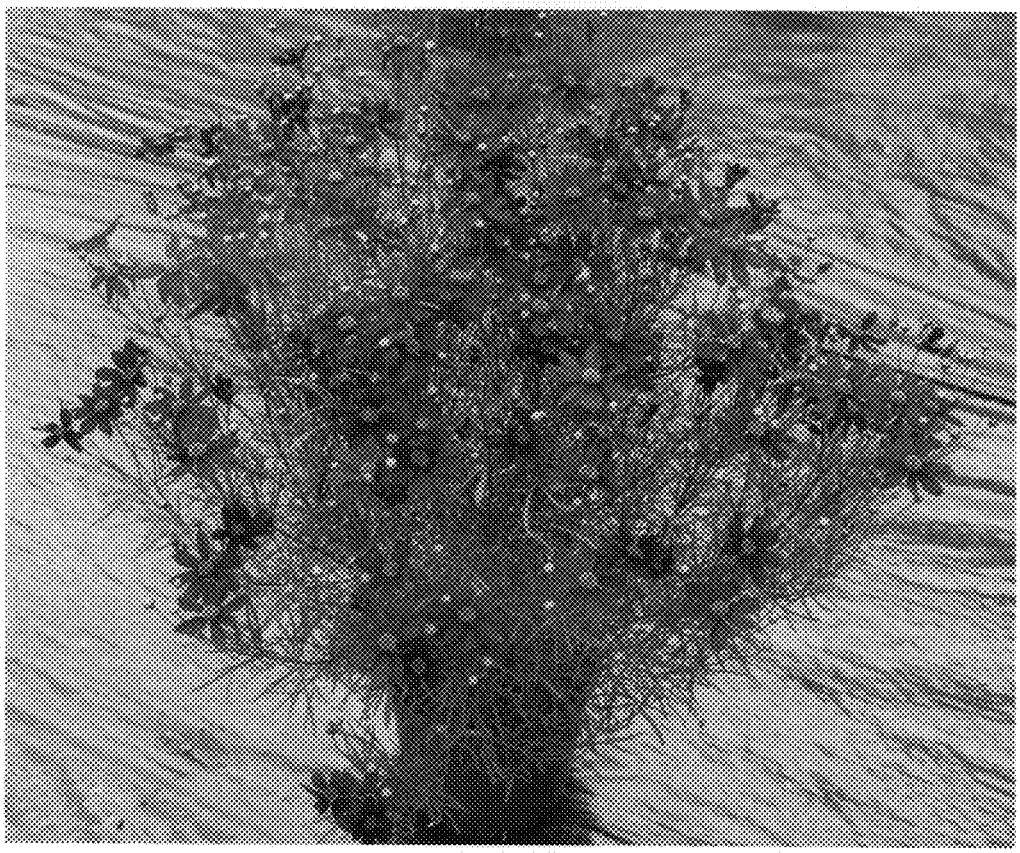
Figure 2:
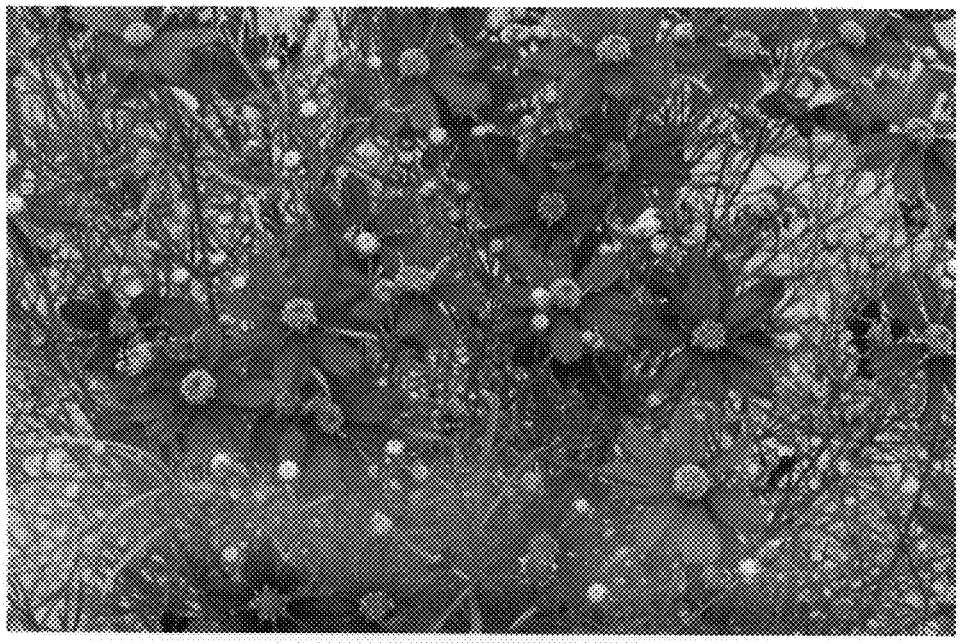

The photograph in FIG. 2 provides a close-up view of the inflorescences of 'Red Satin'.

Figure 3:
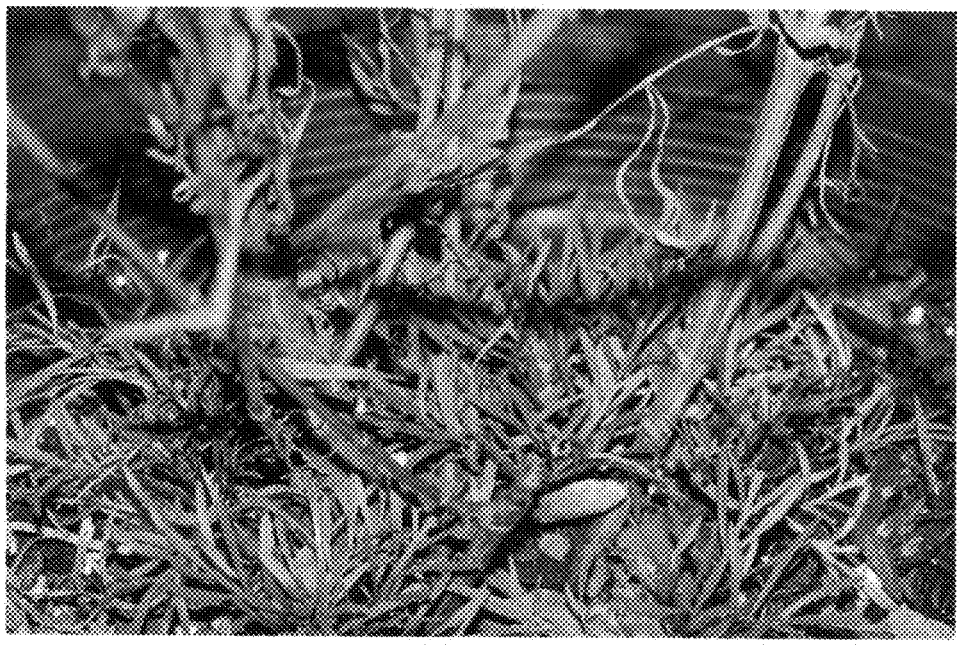

The photograph in FIG. 3 was taken of a two-year old plant as grown outdoors in a 3-gallon container in Hubbardston, Mass. and provides a view of the formation of the leaf rosette arising from the rhizomes formed for overwintering. The colors in the photograph may differ slightly from the color values cited in the detailed botanical description, which accurately describe the colors of the new *Coreopsis*.

DETAILED BOTANICAL DESCRIPTION

The following is a detailed description of nine month-old plants of the new cultivar as grown outdoors in one-gallon containers in Kensington, Conn. and of two year-old plants of the new cultivar as grown outdoors in 3-gallon containers in Hubbardston, Mass. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms from early July until frost in central Massachusetts if sheared lightly once or twice during the growing season.

*Plant habit*.—Herbaceous perennial, clump forming, sturdy, upright and spreading (taller than wide).

*Height and spread*.—An average of 53 cm in height and 41 cm in width.

*Cold hardiness*.—At least in U.S.D.A Zone 5.

*Diseases resistance*.—Has been observed to be more resistant to powdery mildew than is typical of other cultivars of *Coreopsis* early in the growing season due to its lack of seed production, can be susceptible to powdery mildew late in the season.

*Root description*.—Fibrous from rhizomes.

*Propagation*.—Terminal stem cuttings (preferred), division also possible.

*Growth rate*.—Moderate.

Stem description:

*Shape*.—Oval, ridged.

*Stem color*.—Young; a blend of 137A and N138B, mature (woody); a mix of 165A and 197A.

*Stem size*.—Main stems; an average of 46 cm in length (excluding terminal peduncle) and 7 mm in width, secondary; average of 10 cm in length and 4 mm in width, tertiary; 8.5 cm in length and 1 mm in width.

*Stem surface*.—Glabrous and dull.

*Stem aspect*.—Upright to outward.

*Branching habit*.—Well-branched, an average of 18 main branches, 2 secondary branches per main stem, tertiary branches 4.

*Internode length*.—An average of 5 cm.

Foliage description:

*Leaf division*.—Simple.

*Leaf margins*.—Entire to trifid.

*Leaf size*.—Variable, up to 7 cm in length and 2 mm in width when entire, up to 7 cm in length and 3.5 cm in width when tri-fid.

*Leaf shape*.—Linear-narrowly oblanceolate when entire, Linear-narrowly oblanceolate lobes when tri-fid.

*Leaf base*.—Truncate to stem.

*Leaf apex*.—Acute.

*Leaf venation*.—Pinnate, not prominent, matches leaf color on upper and lower surface.

*Leaf attachment*.—Sessile.

*Leaf arrangement*.—Opposite.

*Leaf surface*.—Glabrous on upper and lower surface.

*Leaf color*.—Young and mature upper surface; N137A, young and mature lower surface; 137B.

Inflorescence description:

*Inflorescence type*.—Composite with a single row of ray florets surrounding disk florets in the center, forming a radiant head, inflorescences are borne on branch terminals in loose corymbs.

*Lastingness of inflorescence*.—An average of 10 days until senescence of ray florets, longer in cool temperatures, bracts and disk flowers are persistent.

*Fragrance*.—None detected.

*Quantity of inflorescences*.—An average of 50 per main branch.

*Inflorescence size*.—Corymbs; an average of 8 cm in length and 7.5 cm in width, composite; an average of 1 cm in depth and up to 4.5 cm in diameter.

*Inflorescence buds*.—Average of 5 cm in depth and in diameter, spherical in shape, color; a mix of 16B, 22A and 165A.

*Peduncle*.—Average of 6.5 cm in length and 2 mm in width, glabrous surface, 138A in color.

*Pedicle*.—Average of 5 cm in length and 1 mm in width, glabrous surface, 138B in color.

*Sepals*.—Average of 8, 3 mm in length and 2 mm in width, color; blend of 17A and 8C, slightly translucent in color.

Involucral bracts:

*Bract number*.—9 total, 4 outer bracts and 5 inner bracts.

*Bract arrangement*.—Outer bracts are un-fused and held slightly upward, inner bracts surround receptacle with a campanulate form with apical portion un-fused, spreading, and held close to lower surface of ray florets.

*Bract size*.—Outer bracts; an average of 3 mm in length and 1 mm in width, inner bracts; up to 3 mm in length and 1 mm in width with free portion an average of 2 mm in length and 1 mm in width.

*Bract color*.—Inner bracts; 141A, margins 149C, outer bracts; 143B, tip 141A, margins 149C.

*Bract texture*.—Glabrous on outer and inner surfaces of outer and inner bracts.

*Bract apex*.—Acute on outer and inner bracts.

*Bract base*.—Truncate on inner and outer bracts.

*Bract margins*.—Entire.

*Bract shape*.—Outer bracts; lanceolate, inner bracts; narrowly elliptic.

Ray florets (sterile):

*Number*.—An average of 8 arranged primarily in one row.

*Shape*.—Oblong.

*Size*.—An average of 2 cm in length and 7 mm in width.

*Apex*.—2 notched.

*Base*.—Acute.

*Margins*.—Entire with apex notched.

*Aspect*.—Held horizontal to slightly upward.

*Texture*.—Glabrous and satiny on upper surface, glabrous on lower surface.

*Color*.—When opening inner surface; 187B, tip 10A, base 187A, when opening outer surface; a blend of 7A (more so from mid section to tip) and 187A (more so at the base), when fully open upper surface; 45A with an overlay of 187A, when fully open lower surface; mid section to tip is 4D with streaks of 4A, base to mid section is 183A with specks of 187A.

Disk flowers (perfect):

*Shape*.—Tubular, corolla is fused, flared at apex.

*Number*.—About 80.

*Size*.—About 4 mm in length and 1 mm in width.

*Color*.—En masse; 13A, corolla; base of tube is 13A in color, flared portion is 187A and translucent.

*Receptacle*.—About 8 mm in diameter and 2 mm in depth, 8A in color.

Reproductive organs:

*Presence*.—Disk flowers are perfect, ray flowers are sterile.

*Gynoecium*.—1 Pistil, 3 mm in length, style is very fine, translucent and 17D in color, bifid pilose stigma is 17C in color with branches about 0.5 mm in length and recurved, ovary is 1 mm in length, 0.5 mm in width, inferior, and 17D in color.

*Androcoecium*.—5 stamens, fused into tube surrounding style, 1 mm in length and 0.5 mm in width, about 187A in color, pollen is minimal in quantity and N25B in color.

*Fruit/seed*.—Has been observed to be sterile and to lack seed production.

It is claimed:

1. A new and distinct cultivar of *Coreopsis* plant named 'Red Satin' as herein illustrated and described.

* * * * *